United States Patent [19]
Roche

[11] Patent Number: 4,632,111
[45] Date of Patent: Dec. 30, 1986

[54] ACETABULAR CUP POSITIONING APPARATUS

[75] Inventor: Karen M. Roche, Stillwater, Minn.

[73] Assignee: Minnesota Mining and Manufacturing Company, St. Paul, Minn.

[21] Appl. No.: 714,532

[22] Filed: Mar. 21, 1985

[51] Int. Cl.$^4$ .............................................. A61B 17/00
[52] U.S. Cl. ............................. 128/303 R; 128/92 R; 128/92 VY; 128/92 V
[58] Field of Search .............. 128/92 R, 92 E, 92 EC, 128/92 EB, 303 R

[56] References Cited

U.S. PATENT DOCUMENTS

| | | | |
|---|---|---|---|
| 3,859,992 | 1/1975 | Amstutz | 128/92 E |
| 4,305,394 | 12/1981 | Bertuch, Jr. | 128/303 R |
| 4,475,549 | 10/1984 | Oh | 128/303 R |
| 4,528,980 | 7/1985 | Kenna | 128/92 E |

OTHER PUBLICATIONS

Richards Orthopedic Catalog, cover page, pp. 2, 6, 7 (1969).
10/18/82 letter to Karen Roche by Harry E. Groth, M.D. w/attach.
12/8/82 letter to Karen M. Roche from Harry E. Groth, M.D. w/attachments.
1/13/83 letter to Karen Roche from Harry E. Groth, M.D.

*Primary Examiner*—Robert P. Swiatek
*Assistant Examiner*—Cary E. Stone
*Attorney, Agent, or Firm*—Donald M. Sell; James A. Smith; Robert W. Hoke, II

[57] ABSTRACT

Apparatus for positioning a prosthetic acetabular cup within an acetabulum during total hip replacement surgery. The apparatus includes a pusher ball, a pusher arm affixed to the pusher ball, a positioner arm, and a positioner flange affixed to the positioner arm. The apparatus also includes a slot within the flange dimensioned to receive a part of the pusher arm so that the flange can be faced with the pusher ball. The apparatus can affix the flange facing the ball to define a predetermined angle between the pusher arm and the positioner arm. This apparatus also releasably secures the ball generally mated with the acetabular cup, so that the positioner flange and the positioner arm can be released and removed from the remainder of the apparatus while the pusher ball remains within the acetabular cup to maintain uninterrupted pressure on the acetabular cup via the pusher arm.

9 Claims, 3 Drawing Figures

ACETABULAR CUP POSITIONING APPARATUS

BACKGROUND OF THE INVENTION

The invention relates to apparatus for positioning a prosthetic acetabular cup within an acetabulum during total hip replacement surgery.

As part of total hip replacement surgery, a prosthetic acetabular cup is implanted within the human acetabulum to substitute for the socket of the human hip joint. This is usually done to compensate for severe damage of the acetabulum due to disease, trauma, or other factors. A prosthetic femoral component is mated with the acetabular cup component to complete the total hip replacement surgery. In order to achieve optimal performance of the combined acetabular and femoral prostheses, the acetabular cup must be properly positioned in the acetabulum. An improperly positioned acetabular component can lead to dislocations of the hip joint, decreased range of motion, and eventual loosening or failure of both the acetabular and femoral components.

Interoperative placement of the acetabular component can be a surgically demanding task. The orthopedic surgeon must adequately fix the cup in the proper alignment while hampered by limited surgical exposure and relatively few clear reference points. A typical means of fixation is a biocompatible grouting agent such as polymethyl methacrylate bone cement. In order to achieve adequate performance from such a cement, it is necessary to ensure that complete filling is obtained, with minimal voids, air bubbles, etc. This requirement presents another interoperative difficulty for the surgeon; i.e., adequate pressure must be maintained on the prosthetic component during the early stages of cement polymerization while avoiding relative motion between the cup component and the cement. Any rocking or twisting of the cup in the cement can compromise good cement filling, by pulling the soft cement away from the bone or away from the surface of the cup.

Traditional cup positioners generally include at least a pusher ball sized and shaped to fit the recess within the acetabular component, a positioner arm, a positioner flange juxtaposed the pusher ball, and a pusher arm connected to the ball and to the flange to enable the user to push the prosthetic acetabular cup, when resting on the flange, into the prepared acetabulum. Generally, the cup must be manually held against the flange during implantation. In some cases, the cup is aligned on the flange by means of small projecting pins which can engage complementary holes in the face of the cup. Such pins require the surgeon to always select the cup and the cup positioner from the same manufacturer, to ensure that pins and holes will mate properly. While such pins can help to orient the cup relative to the positioner, it is not believed that they prevent the cup from falling off the flange, particularly in the case of heavier metal-backed acetabular components; the cup must still be manually held against the flange as described above. In the case of U.S. Pat. No. 4,475,549, a pusher ball is described at column 2, lines 33-35 as provided with a cover 23 of a compressible material, such as silicone, which has a relatively high coefficient of friction. In order to remove the cup from this frictional fit, a rigid blunt rod, described at column 4, lines 12-15, is required to press against the cup. This change of instruments can, however, disturb the cup in the cement and compromise good cement filling.

Once the cup has been aligned and fully implanted or inserted, the flange has served its purpose and, if left in contact with the cup, can cause the cup to be moved as described above. There is also a risk of the cement bonding to the flange. Further, removing any excess cement from around the periphery of the cup is more difficult when the flange is obscuring the view of the cup. Separate cup pushers are often used in conjunction with a cup positioner to address some of these problems. The positioner is removed once the cup has been placed in the acetabulum, and the pusher is separately used to apply pressure to the cup. However, the possibility exists that this change of instruments will dislodge the cup or rock it in the soft cement. U.S. Pat. No. 4,305,394 addresses this possibility and describes a means for disengaging the flange so that the flange no longer contacts the rim of the cup. The flange is disengaged by means of a trigger mechanism during cement polymerization, but the flange still remains within the surgical field and can obscure the view of the cup.

In addition to the pusher ball, the flange, and the pusher arm, some acetabular cup positioning instruments include means for establishing reference angles to better insure proper alignment of the prosthetic cup. Many traditional positioner designs include a reference arm for establishing the abduction angle. U.S. Pat. No. 4,475,549 further includes means for establishing the anteversion angle. In the case of U.S. Pat. No. 4,475,549, the anteversion angle is established relative to the positioner arm, as described starting in column 3, line 12. This is, it is believed, difficult to accomplish since the line of sight of the physician user is not parallel with or in the same plane as the plane defined by the arms 33 and 35, as best shown in FIG. 5; there can be a tendency to rotate the positioner 11 about the vertical axis shown in FIG. 5 until the handle 51 is aligned with the patient axis 53, thereby adding undesired cup rotation to the anteversion angle.

SUMMARY OF THE INVENTION

The above-described complications of disturbing the acetabular cup in the soft cement, obscuring the view of the cup and of the surgical field generally, and inadvertently altering the anteversion angle are reduced with the apparatus of the present invention. This apparatus permits the physician user to maintain a constant pressure on the cup with one hand while using the other hand to remove the flange and the positioner arm portions of the apparatus after they have served their purpose. Once the flange and the positioner arm portions have been removed, the free hand can be used to remove any excess cement from the periphery of the cup. Further, this apparatus can be used with a wider variety of cups due to a unique, adjustable mechanism that can accommodate cups having varying dimensions and manufacturing tolerances.

According to the invention, there is provided an apparatus suitable for positioning a prosthetic cup within an acetabulum including a pusher ball, a pusher arm, a positioner arm, and a positioner flange. This apparatus also includes means for removably engaging the flange with the pusher arm to face the flange with the pusher ball. This apparatus further includes adjustable means for releasably affixing the flange faced with the ball, to define a predetermined angle between the pusher arm and the positioner arm. This affixing means also releasably secures the ball within the acetabular cup. The pusher ball includes an outer surface adapted to generally mate with a recessed surface within the acetabular cup. The recessed surface of the acetabular cup is dimensioned to mate with a prosthetic femoral head in conventional fashion. The pusher arm includes a first end portion affixed to the pusher ball, an intermediate straight portion, and a second end portion opposite the first end portion. The positioner flange has first and second major opposite surfaces and is preferably adapted to contact the first major surface with a rim portion of the acetabular cup. The positioner arm includes a first end portion affixed to the flange, an intermediate straight portion, and a second end portion opposite the first end portion. The adjustable affixing means affixes the first major surface of the flange faced with the pusher ball along the intermediate portion of the pusher arm and the outer surface of the pusher ball generally mated with the recessed surface of the acetabular cup with the rim portion of the cup preferably contacting the first major surface of the flange, so that the positioner flange and the positioner arm can be released and removed from the intermediate straight portion of the pusher arm while the pusher ball remains within the acetabular cup to maintain uninterrupted pressure on said acetabular cup via the pusher arm.

BRIEF DESCRIPTION OF THE DRAWING

Other advantages of the invention will become apparent from the following drawing wherein like numerals refer to like parts.

DESCRIPTION

Figure 3:
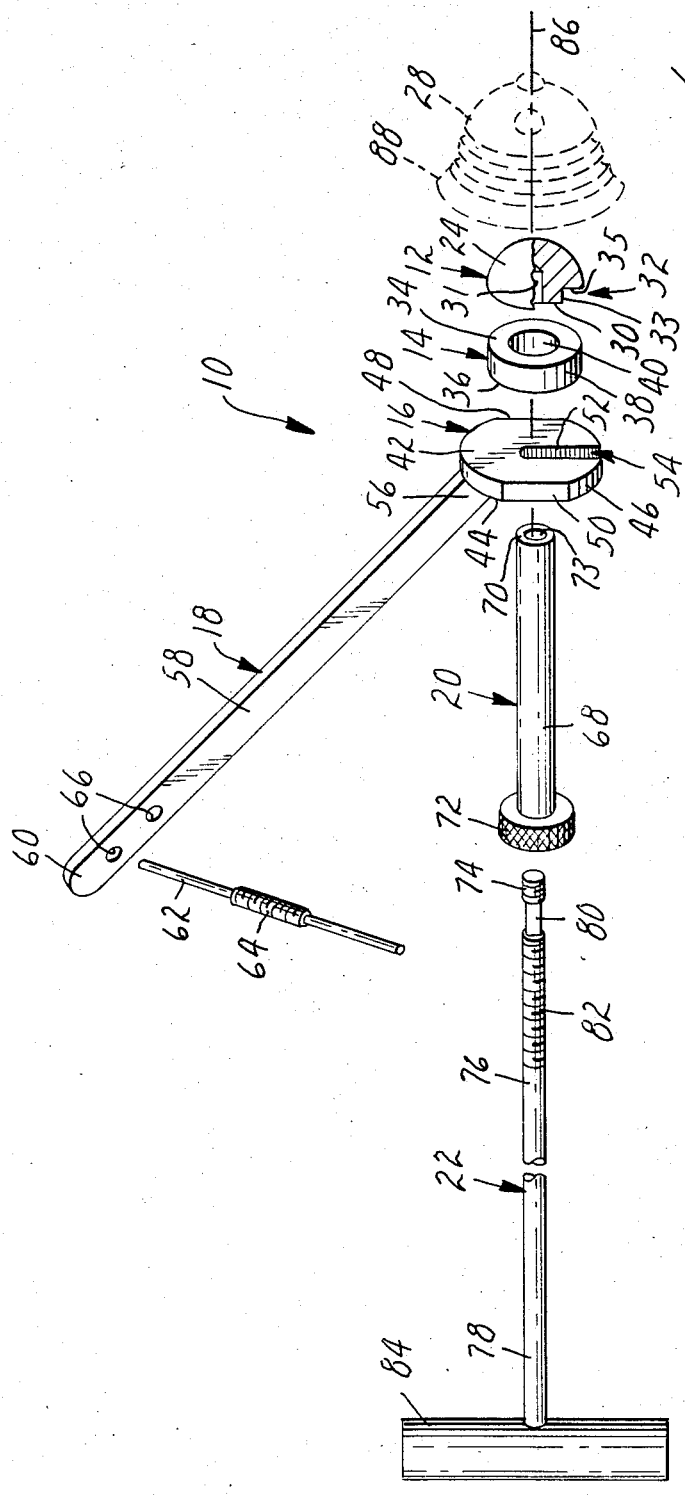
FIG. 3 is an exploded, perspective view, with portions broken away and with portions sectioned, of the acetabular cup positioning apparatus of FIG. 1 with the acetabular cup of FIG. 2 again shown in phantom line representation.

Referring now to the figures of the drawing and in particular to FIG. 3, there is shown in perspective view a preferred acetabular cup positioning apparatus 10 of the present invention. The apparatus 10 is generally comprised of a pusher ball 12, an elastomeric annular collar 14, positioner flange 16, a positioner arm 18, a 1 retainer nut 20 and a pusher arm 22. All of the aforegoing are preferably comprised of type 304 stainless steel, except the collar 14 which is preferably comprised of a low durometer silicone rubber. A suitable silicone rubber is Dow Corning MDX-4-4210 clean grade elastomer.

Figure 1:
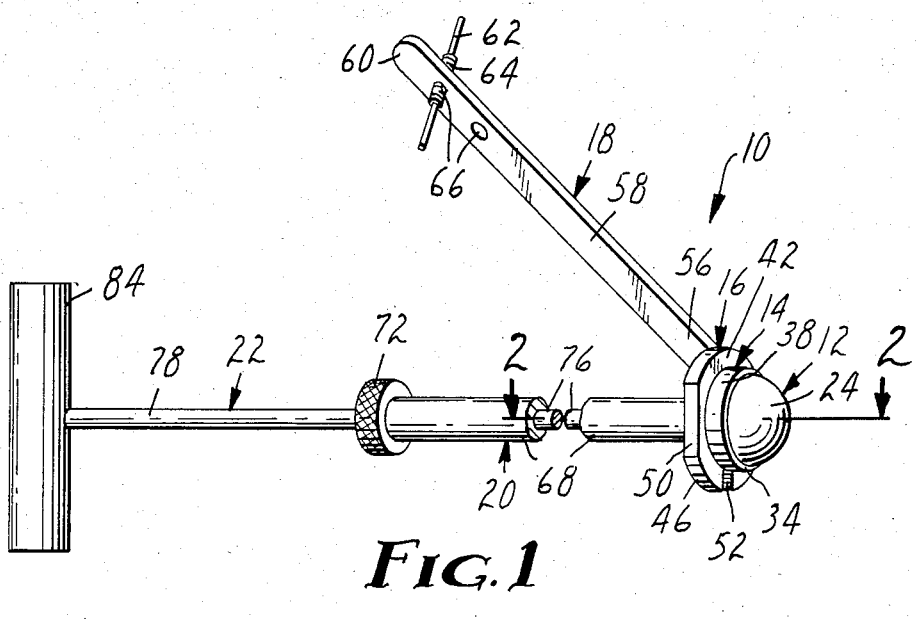
FIG. 1 is a perspective view of an acetabular cup positioning apparatus of the present invention with portions broken away.
Figure 2:
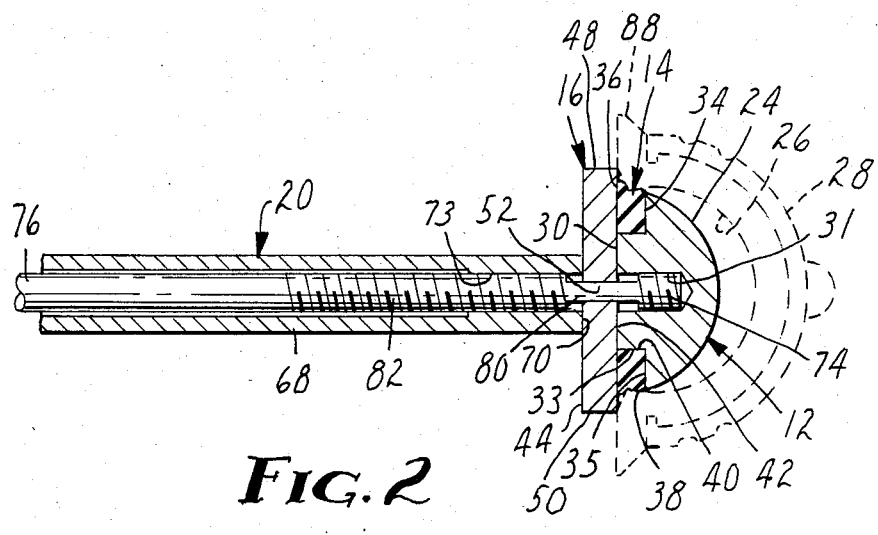
FIG. 2 is an enlarged, cross-sectional view of the acetabular cup positioning apparatus of FIG. 1 taken approximately along the line 2—2 of FIG. 1 with portions broken away and with an acetabular cup added in phantom line representation.

The pusher ball 12 preferably includes a part spherical outer surface 24 adapted to generally mate with a part spherical recessed surface 26 within an acetabular cup 28. The cup 28 is shown in phantom line representation in FIGS. 2 and 3. The recessed surface 26 within the cup 28 is best seen in FIG. 2. The recessed surface 26 is dimensioned to receive a conventional prosthetic femoral head, not shown. The pusher ball 12 further includes a planar surface 30, a threaded recess 31, and an undercut annular lip 32. The annular lip 32 is defined by two orthogonally arranged annular surfaces 33 and 35 which connect the outer surface 24 with the planar surface 30.

The elastomeric annular collar 14 includes first and second major, opposite surfaces 34 and 36, an outer cylindrical surface 38 and an inner cylindrical surface 40. The surface 36 is shown in FIG. 2. The inner cylindrical surface 40 is dimensioned to generally mate with the annular surface 33 of the pusher ball 12 to abut the first major surface 34 of the collar 14 with the surface 35 of the lip 32 when the elastomeric annular collar 14 is received within the annular lip 32. Further, when the collar 14 is so received, the surface 36 projects from the lip 32 in a manner and for a purpose to be explained below.

The positioner flange 16 includes first and second major, opposite surfaces 42 and 44 and a connecting edge surface 46, as best shown in FIG. 2, providing the flange 16 with a generally circular, disc-like or cylindrical shape. The circular, disc-like shape is broken up by a pair of preferably planar and parallel edge surface portions 48 and 50 and an inwardly extending edge surface portion 52. The inwardly extending edge surface portion 52 extends from a first location on the periphery of the circular, disc-like portion of the edge surface 46 generally to the center of the flange 16 in a plane parallel to the planar edge surface portions 48 and 50 and back to a second location on the periphery of the circular, disc-like portion of the edge surface 46 to define a radially extending slot 54 within the flange 16. The slot 54 is dimensioned to receive a portion of the pusher arm 22.

The positioner arm 18 includes a first end portion 56 affixed to the flange 16, an intermediate straight portion 58 defining a predetermined angle lying between the positioner arm 18 and the pusher arm 22 when these two arms 18 and 22 are affixed in a manner to be explained, and a second end portion 60 opposite the first end portion 56. The second end portion 60 preferably includes an anteversion pin 62. The pin 62 is provided with an intermediate threaded portion 64 which complementarily mates with either of two threaded through portions 66 of the second end portion 60. One of the threaded portions 66 is identified with an "R" and is used in determining the proper anteversion angle during a right hip surgical procedure and the other is identified with an "L" and is used in determining the proper anteversion angle during a left hip surgical procedure. The manner in which this is done will be explained below.

The retainer nut 20 includes a cylindrical stand off portion 68 having a contact surface 70 and a knurled grip portion 72. The retainer nut 20 has a threaded through bore portion 73 which receives the pusher arm 22. The pusher arm 22 includes a first end threaded portion 74 which is dimensioned to complementarily mate with the threaded recess 31 within the pusher ball 12 so that the pusher arm 22 can be affixed to the pusher ball 12. The pusher arm 22 also includes an intermediate straight portion 76 and a second end portion 78 which is opposite the first end portion 74. The intermediate straight portion 76 preferably includes a flattened part 80 which is dimensioned to be received within the slot 54 within the flange 16 to face the first major surface 42 of the flange 16 with the pusher ball 12 along the intermediate portion 76 of the pusher arm 22. The intermediate straight portion 76 further includes a threaded part 82 which is dimensioned to complementarily mate with the threaded through bore portion 73 of the retainer nut 20 so that the retainer nut 20 can be movably mounted on the pusher arm 22 for a purpose to be described. The second end portion 78 is preferably provided with a conventional handle portion 84. The handle portion 84 preferably lies in the plane formed by pusher arm 22 and positioner arm 18.

Prior to use during total hip replacement surgery, the apparatus 10 must be assembled, and the acetabular cup 28 properly affixed thereto. This assembly will next be described principally in conjunction with FIG. 3 of the drawing. The anteversion pin is screwed into one of the two threaded through portions 66 of the positioner arm 18 to establish the proper anteversion angle for a right or left total hip replacement, as the case may be. The threaded through portions 66 are oriented within the positioner arm 18 to define an angle between the straight anteversion pin 62 and the straight intermediate portion 76 of the pusher arm 22 of between 65 and 75 degrees and preferably about 70 degrees, as measured from the plane formed by the pusher arm 22, the positioner arm 18, and the handle portion 84. More specifically, the pin 62 lies in a plane that is parallel to a reference plane. The reference plane includes the pusher arm and is perpendicular to the earlier-described plane formed by the pusher arm 22, the positioner arm 18, and the handle portion 84. The pin 62 intersects the plane of the pusher arm 22, the positioner arm 18, and the handle portion 84 at the preferred angle of 70 degrees to provide a preferred anteversion angle of 20 degrees.

The retainer nut 20 is screwed onto the threaded part 82 of the pusher arm 22. This can be accomplished by screwing the retainer nut 20 through the first end threaded portion 74 of the pusher arm 22 or by merely passing portion 74 through the nut 20, depending upon the dimensions of the portion 74. The portion 74 is next passed through the elastomeric annular collar 14 and screwed into the threaded recess 31 within the pusher ball 12.

The positioner arm 18 is engaged with the pusher arm 22 by sliding the flattened part 80 of the pusher arm 22 within the slot 54 of the flange 16 and positioning the flange 16 between the elastomeric annular collar 14 and the retainer nut 20 with the first major surface 42 of the flange 16 generally facing the pusher ball 12 and the second major surface 44 of the flange 16 generally facing the retainer nut 20. The elastomeric annular collar 14 is received within the undercut annular lip 32 of the pusher ball 12 to juxtapose the one major surface 34 of collar 14 with annular surface 35 of lip 32 and inner cylindrical surface 40 of collar 14 with annular surface 33 of lip 32. In this position, the inner cylindrical surface 40 extends beyond surface 33 to project the major surface 36 of the collar 14 beyond the lip 32 in a plane generally normal to a long axis 86 of the apparatus 10; i.e., in a plane generally parallel with the first major surface 42 of the flange 16 when the surface 42 is faced with the pusher ball 12 as earlier described.

Next, the retainer nut 20 is screwed towards the flange 16 until the flange 16 is pressed against the elastomeric annular collar 14, which is received within the lip 32. The part spherical outer surface 24 of the pusher ball 12 is received within the recessed surface 26 within the acetabular cup 28, and the nut 20 is adjusted until the elastomeric annular collar 14 is forced radially outward from the lip 32 to press the outer cylindrical surface 38 of the collar 14 against the recessed surface 26 and thereby affix the acetabular cup 28 with the pusher ball 12. A rim portion 88 of the cup 28 is preferably contacted with the first major surface 42 of the flange 16, as best shown in FIG. 2, to facilitate cup positioning by providing a flat surface parallel to the face of the cup 28. Also, as the nut 20 is tightened as just described, the flange 16 is affixed relative to the pusher arm 22 to define an abduction angle lying between the intermediate straight portion 58 of the positioner arm 18 and the intermediate straight portion 76 of the pusher arm 22 in the range of 30 to 45 degrees. Preferably, the angle of abduction is approximately 45 degrees.

In addition to establishing the abduction angle, tightening the nut 20 against the flange 16 fixes the relative positions of the two arms 18 and 22 and thereby provides the reference for the anteversion angle for a right or a left hip as already described. Hence, the acetabular cup 28 is oriented relative to the apparatus 10 in two planes, and if the cup 28 is symmetrical, as shown, this orients the cup 28 relative to the apparatus in all three planes. Generally, the axis of the cup 28 will coincide with the axis 86.

Once the acetabular cup 28 is secured to the apparatus 10 and oriented as just described, the acetabular cup 28 can be inserted and aligned in a human acetabulum conventionally prepared with a suitable bone cement. The cup 28 must be anatomically aligned prior to its insertion in the acetabulum. This is accomplished by first aligning the long axis 86 of the pusher arm 22 with the long axis of the patient's torso. Next, the plane which is defined by the pusher arm 22, the T-handle 84 of the pusher arm 22, and the positioner arm 18 is rotated until it is aligned with the coronal plane of the patient. The cup 28 and the apparatus 10 are moved directly in front of the acetabulum during this portion of the alignment. The apparatus 10 is then rotated in the coronal plane of the patient until the positioner arm 18 is perpendicular to the long axis of the patient's torso. The direction of rotation is dependent upon the surgical exposure utilized and upon whether a left or right hip surgery is being performed. This direction is within the knowledge of one skilled in the art. This motion establishes the correct abduction angle. Next, with the guide pin 62 within one of the threaded holes 66 for a left or a right hip surgery, the apparatus 10 is rotated until the pin 62 is perpendicular to the coronal plane of the patient. This motion is equivalent to rotating the pusher arm 22 out of the coronal plane, in the sagittal plane, toward the head of the patient. This motion establishes the correct angle of anteversion. When the surgeon is satisfied that proper alignment has been achieved, the cup 28 is pushed firmly and directly into the acetabulum along the axis 86. Visualization of the cup 28 is aided by the planar edge surface portions 48 and 50 of the flange 16. The portions 48 and 50 expose the rim portion 88 of the cup 28 and afford the physician user a better view of the cup 28 in relation to the apparatus 10 and the acetabulum.

Once the cup 28 is fully seated within the acetabulum, the positioner arm 18 and flange 16 are removed in the following manner. While maintaining firm axial pressure on the pusher arm 22 via the handle 84, the retaining nut 20 is gently backed off by rotating it in a counterclockwise direction for several turns. After this is done, the flange 16 is pulled straight back for a short distance, and then separated from the pusher arm 22 and subsequently removed from the surgical field altogether, while axial pressure is still maintained through the pusher arm 22. Removal of the flange 16 releases the elastomeric annular collar 14, which can be pulled gently from the recess of the cup 28 with a forceps, if it does not pull out of the cup 28 with removal of the flange 16. At this point only the spherical outer surface 24 of the pusher ball 12 is in contact with the cup 28. Axial pressure is maintained via the handle 84 of the pusher arm 22 for an additional three to four minutes, or until the surgeon has determined that the cement has hardened sufficiently. At this point the pusher arm 22 is removed from the cup 28 along with the elastomeric annular collar 14, and the surgery continues in the normal manner.

Although an exemplary embodiment of the invention has been shown and described, many changes, modifications, and substitutions can be made by one having ordinary skill in the art without necessarily departing from the spirit and the scope of this invention.

What is claimed:

1. Apparatus suitable for positioning a prosthetic acetabular cup within an acetabulum, said cup having a recessed surface dimensioned to mate with a prosthetic femoral head, said apparatus comprising:
A. a pusher ball, for pressing the acetabular cup into the acetabulum, said pusher ball including an outer surface adapted to generally mate with said recessed surface of said acetabular cup;
B. a pusher arm including:
  (1) a first end portion affixed to said pusher ball;
  (2) an intermediate straight portion; and
  (3) a second end portion opposite said first end portion;
C. a positioner flange having first and second major opposite surfaces;
D. a positioner arm including:
  (1) a first end portion affixed to said flange;
  (2) an intermediate straight portion; and
  (3) a second end portion opposite said first end portion; and
E. means for removably engaging said flange with said intermediate straight portion of said pusher arm to face said first major surface of said flange with said pusher ball along said intermediate straight portion of said pusher arm, said removable engaging means comprising an edge surface connecting said first and second major surfaces of said flange and a portion of said edge surface extending from a first location on the periphery of said major surfaces generally to the center of said major surfaces and back to a second location on the periphery of said major surfaces to define a slot dimensioned to receive a part of said intermediate portion of said pusher arm; and
F. adjustable means for releasably affixing:
  (1) said flange faced with said pusher ball to define a predetermined angle between said intermediate straight portions of said pusher arm and said positioner arm; and
  (2) said outer surface of said pusher ball generally mated with said recessed surface of said acetabular cup, so that said positioner flange and said positioner arm can be released and removed from said intermediate straight portion of said pusher arm while said pusher ball remains mated with said recessed surface of said acetabular cup to maintain uninterrupted pressure on said acetabular cup.

2. The apparatus according to claim 1 wherein said adjustable affixing means comprises:
A. said pusher ball further including a lip;
B. an elastomeric collar dimensioned to be received within said lip of said pusher ball with a major surface of said collar projecting from said lip in a plane generally parallel with said first major surface of said flange when said first major surface of said flange is faced with said pusher ball; and
C. means for releasably pressing said first major surface of said flange against said major surface of said elastomeric collar to force said elastomeric collar outwards from said lip and against said recessed surface of said acetabular cup to releasably secure said acetabular cup to said pusher ball.

3. The apparatus according to claim 2 wherein said releasable pressing means comprises:
A. a threaded part of said intermediate portion of said pusher arm located between said part of said intermediate portion to be received within said slot and said second end portion of said pusher arm; and
B. a retainer nut having a threaded portion receiving and mating with said threaded part so that said retainer nut can contact said second major surface of said flange and press said first major surface of said flange against said major surface of said elastomeric collar and force said elastomeric collar radially outwards.

4. The apparatus according to claim 1 further comprising:
A. an anteversion pin; and
B. means for affixing said anteversion pin with said second end portion of said positioner arm to define a predetermined angle between said anteversion pin and said intermediate portion of said pusher arm when said flange is affixed to said pusher arm.

5. Apparatus suitable for positioning a prosthetic acetabular cup within an acetabulum, said cup having a recessed surface dimensioned to mate with a prosthetic femoral head, said apparatus comprising:
A. a pusher ball, for pressing the acetabular cup into the acetabulum, said pusher ball including an outer surface adapted to generally mate with said recessed surface of said acetabular cup;
B. a pusher arm-including:
  (1) a first end portion affixed to said pusher ball;
  (2) an intermediate straight portion; and
  (3) a second end portion opposite said first end portion;
C. a positioner flange having first and second major opposite surfaces;
D. a positioner arm including:
  (1) a first end portion affixed to said flange;
  (2) an intermediate straight portion; and
  (3) a second end portion opposite said first end portion; and
E. means for removably engaging said flange with said pusher arm to face said first major surface of said flange with said pusher ball along said intermediate straight portion of said pusher arm, said removable engaging means comprising an edge surface connecting said first and second major surfaces of said flange and a portion of said edge surface extending from a first location on the periphery of said major surfaces generally to the center of said major surfaces and back to a second location on the periphery of said major surfaces to define a slot dimensioned to receive a part of said intermediate portion of said pusher arm; and
F. adjustable means for releasably affixing:
  (1) said flange faced with said pusher ball to define a predetermined angle between said intermediate straight portions of said pusher arm and said positioner arm; and (2) said outer surface of said pusher ball generally mated with said recessed surface of said acetabular cup, so that said positioner flange and said positioner arm can be released and removed from said intermediate straight portion of said pusher arm while said pusher ball remains mated with said recessed surface of said acetabular cup to maintain uninterrupted pressure on said acetabular cup.

6. Apparatus suitable for positioning a prosthetic acetabular cup within an acetabulum, said cup having a recessed surface dimensioned to mate with a prosthetic femoral head, said apparatus comprising:
A. a pusher ball, for pressing the acetabular cup into the acetabulum, said pusher ball including an outer surface adapted to generally mate with said recessed surface of said acetabular cup;
B. a pusher arm including:
   (1) a first end portion affixed to said pusher ball;
   (2) an intermediate straight portion; and
   (3) a second end portion opposite said first end portion;
C. a positioner flange having first and second major opposite surfaces;
D. a positioner arm including:
   (1) a first end portion affixed to said flange;:
   (2) an intermediate straight portion; and
   (3) a second end portion opposite said first end portion; and
E. means for removably engaging said flange with said pusher arm to face said first major surface of said flange with said pusher ball along said intermediate straight portion of said pusher arm; and
F. adjustable means for releasably affixing said flange faced with said pusher ball to define a predetermined angle between said intermediate straight portions of said pusher arm and said positioner arm and for releasably affixing said outer surface of said pusher ball generally mated with said recessed surface of said acetabular cup, so that said positioner flange and said positioner arm can be released and removed from said intermediate straight portion of said pusher arm while said pusher ball remains mated with said recessed surface of said acetabular cup to maintain uninterrupted pressure on said acetabular cup, said adjustable affixing means comprising:
   (1) said pusher ball further including a lip;
   (2) an elastomeric collar dimensioned to be received within said lip of said pusher ball with a major surface of said collar projecting from said lip in a plane generally parallel with said first major surface of said flange when said first major surface of said flange is faced with said pusher ball; and
   (3) means for releasably pressing said first major surface of said flange against said major surface of said elastomeric collar to force said elastomeric collar outwards from said lip and against said recessed surface of said acetabular cup to releasably secure said acetabular cup to said pusher ball.

7. The apparatus according to claim 6 wherein said releasable pressing means comprises:
A. a threaded part of said intermediate portion of said pusher arm located between said part of said intermediate portion to be received within said slot and said second end portion of said pusher arm; and
B. a retainer nut having a threaded portion receiving and mating with said threaded part so that said retainer nut can contact said second major surface of said flange and press said first major surface of said flange against said major surface of said elastomeric collar and force said elastomeric collar radially outwards.

8. Apparatus suitable for positioning a prosthetic acetabular cup within an acetabulum, said cup having a recessed surface dimensioned to mate with a prosthetic femoral head, said apparatus comprising:
A. a pusher ball, for pressing the acetabular cup into the acetabulum, said pusher ball including an outer surface adapted to generally mate with said recessed surface of said acetabular cup;
B. a pusher arm including:
   (1) a first end portion affixed to said pusher ball;
   (2) an intermediate straight portion; and
   (3) a second end portion opposite said first end portion;
C. a positioner flange having first and second major opposite surfaces;
D. a positioner arm including:
   (1) a first end portion affixed to said flange;
   (2) an intermediate straight portion; and
   (3) a second end portion opposite said first end portion; and
E. means for removably engaging said flange with said pusher arm to face said first major surface of said flange with said pusher ball along said intermediate straight portion of said pusher arm;
F. adjustable means for releasably affixing:
   (1) said flange faced with said pusher ball to define a predetermined angle between said intermediate straight portions of said pusher arm and said positioner arm; and
   (2) said outer surface of said pusher ball generally mated with said recessed surface of said acetabular cup, so that said positioner flange and said positioner arm can be released and removed from said intermediate straight portion of said pusher arm while said pusher ball remains mated with said recessed surface of said acetabular cup to maintain uninterrupted pressure on said acetabular cup;
G. an anteversion pin; and
H. means for affixing said anteversion pin with said second end portion of said positioner arm to define a predetermined angle between said anteversion pin and said intermediate portion of said pusher arm when said flange is affixed to said pusher arm.

9. Apparatus suitable for positioning a prosthetic acetabular cup within an acetabulum, said cup having a recessed surface dimensioned to mate with a prosthetic femoral head, said apparatus comprising:
A. a pusher ball, for pressing the acetabular cup into the acetabulum, said pusher ball including an outer surface adapted to generally mate with said recessed surface of said acetabular cup;
B. a pusher arm including:
   (1) a first end portion affixed to said pusher ball;
   (2) an intermediate straight portion; and
   (3) a second end portion opposite said first end portion;
C. a positioner flange having first and second major opposite surfaces;
D. a positioner arm including:
   (1) a first end portion affixed to said flange;
   (2) an intermediate straight portion;
   (3) a second end portion opposite said first end portion; and (4) means for visualizing said acetabular cup when said pusher ball is affixed generally mated with said recessed surface of said acetabular cup;

E. means for removably engaging said flange with said pusher arm to face said first major surface of said flange with said pusher ball along said intermediate straight portion of said pusher arm; and F. adjustable means for releasably affixing:
  (1) said flange faced with said pusher ball to define a predetermined angle between said intermediate straight portions of said pusher arm and said positioner arm; and
  (2) said outer surface of said pusher ball generally mated with said recessed surface of said acetabular cup, so that said positioner flange and said positioner arm can be released and removed from said intermediate straight portion of said pusher arm while said pusher ball remains mated with said recessed surface of said acetabular cup to maintain uninterrupted pressure on said acetabular cup.

* * * * *